United States Patent
Kersey et al.

(10) Patent No.: US 10,379,071 B2
(45) Date of Patent: Aug. 13, 2019

(54) DUAL ACOUSTIC AND ELECTRICAL ANALYSIS TECHNIQUE FOR THE TOMOGRAPHIC DETERMINATION OF MULTIPHASE FLOWS IN PIPES AND/OR LIQUID/FROTH INTERFACES IN PROCESS TANKS

(71) Applicants: Alan D. Kersey, South Glastonbury, CT (US); Christian V. O'Keefe, Durham, CT (US)

(72) Inventors: Alan D. Kersey, South Glastonbury, CT (US); Christian V. O'Keefe, Durham, CT (US)

(73) Assignee: CiDRA Corporate Services Inc., Wallingford, CT (US)

( * ) Notice: Subject to any disclaimer, the term of this patent is extended or adjusted under 35 U.S.C. 154(b) by 1241 days.

(21) Appl. No.: 14/380,209

(22) PCT Filed: Feb. 28, 2013

(86) PCT No.: PCT/US2013/028285
§ 371 (c)(1),
(2) Date: Aug. 21, 2014

(87) PCT Pub. No.: WO2013/130783
PCT Pub. Date: Sep. 6, 2013

(65) Prior Publication Data
US 2015/0020579 A1    Jan. 22, 2015

Related U.S. Application Data

(60) Provisional application No. 61/604,080, filed on Feb. 28, 2012.

(51) Int. Cl.
*G01N 27/06* (2006.01)
*G01N 27/08* (2006.01)
(Continued)

(52) U.S. Cl.
CPC ............ *G01N 27/08* (2013.01); *G01N 27/06* (2013.01); *G01N 29/024* (2013.01);
(Continued)

(58) Field of Classification Search
CPC ....... G01B 17/025; A21B 5/682; A61B 18/02; G01N 27/08; G01N 27/06; G01N 29/024; G01N 29/0672
(Continued)

(56) References Cited

U.S. PATENT DOCUMENTS

| 4,328,707 A | 5/1982 | Clement et al. |
| 4,331,021 A | 5/1982 | Lopez et al. |

(Continued)

FOREIGN PATENT DOCUMENTS

| WO | 2013028870 | 2/2013 |
| WO | 2013059458 | 4/2013 |

OTHER PUBLICATIONS

L. M. Heikkinen Real Time Three-dimensional Electrical Impedance Tomography, pp. 540-545 (Year: 2006).*
(Continued)

*Primary Examiner* — Regis J Betsch
*Assistant Examiner* — Kaleria Knox
(74) *Attorney, Agent, or Firm* — Ware, Fressola, Maguire & Barber LLP

(57) ABSTRACT

Apparatus is provided featuring a signal processor or processing module configured to: receive signaling containing information about at least two sensing modalities sensed by a single probe arranged in relation to a multiphase flow or process volume; and determine using a multiple modality tomographic analysis technique information about different fluid layers in the multiphase flow or process volume, based at least partly on the signaling received. The signal processor or processing module may be configured to provide corre-
(Continued)

sponding signaling containing corresponding information about different fluid layers in the multiphase flow or process volume.

30 Claims, 3 Drawing Sheets

(51) Int. Cl.
*G01N 29/06* (2006.01)
*G01N 29/07* (2006.01)
*G01N 33/26* (2006.01)
*G01N 29/024* (2006.01)

(52) U.S. Cl.
CPC ......... *G01N 29/0672* (2013.01); *G01N 29/07* (2013.01); *G01N 33/26* (2013.01); *G01N 2291/011* (2013.01); *G01N 2291/024* (2013.01); *G01N 2291/0224* (2013.01); *G01N 2291/02433* (2013.01); *G01N 2291/02836* (2013.01); *G01N 2291/02863* (2013.01)

(58) Field of Classification Search
USPC .................. 73/861.25; 600/439, 587; 606/21
See application file for complete search history.

(56) References Cited

U.S. PATENT DOCUMENTS

| | | | |
|---|---|---|---|
| 4,386,854 A | 6/1983 | Byer | |
| 5,181,778 A | 1/1993 | Beller | |
| 6,078,397 A | 6/2000 | Monchalin et al. | |
| 7,410,484 B2* | 8/2008 | Littrup ................... | A61B 18/02 606/21 |
| 7,673,525 B2* | 3/2010 | Huang ................. | G01B 17/025 73/861.25 |
| 8,066,641 B2* | 11/2011 | Barthe ................... | A61B 5/682 600/439 |
| 2003/0036713 A1* | 2/2003 | Bouton .................... | A61B 5/05 600/587 |
| 2003/0160622 A1 | 8/2003 | Duensing et al. | |

OTHER PUBLICATIONS

G Steiner "A bio-electromechanical imaging technique with combined electrical impedance and ultrasound tomography", pp. S63-S75 (Year: 2008).*
Kunyansky "A mathematical model and inversion procedure for magneto-acousto-electric tomography", pp. 1-21 (Year: 2011).*

* cited by examiner

Apparatus 10

Signal processor or signal processing module 10a configured to receive signaling containing information about at least two sensing modalities sensed by a single probe arranged in relation to a multiphase flow or process volume; and determine using a multiple modality tomographic analysis technique information about different fluid layers in the multiphase flow or process volume, based at least partly on the signaling received.

Other modules 10b for implementing the signal processing functionality, including a memory module, data and control busing architecture and input/output modules.

Figure 1

Figure 2: Concept of using two sensing modalities on a single probe to provide enhanced tomographic imaging Figure 3: Principle of Operation
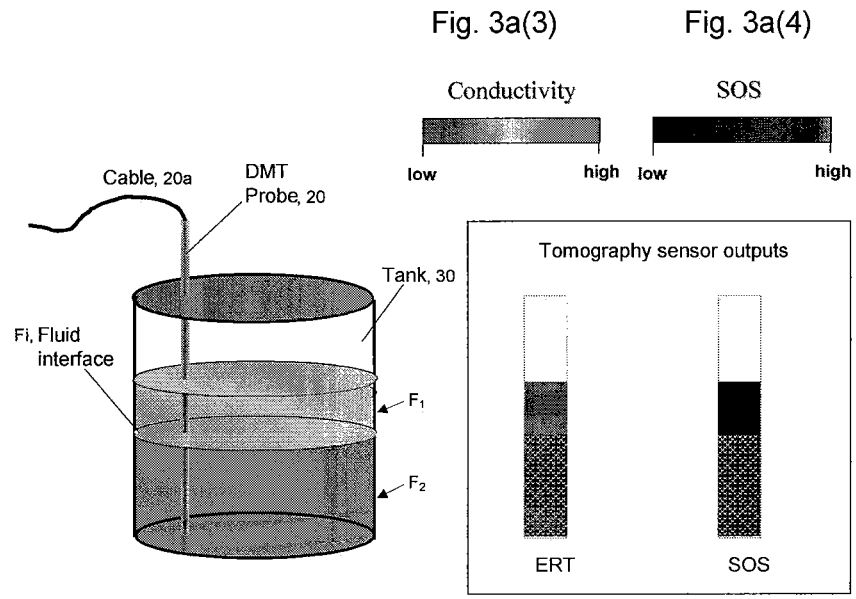
Fig. 3a(1)  Fig. 3a(2)
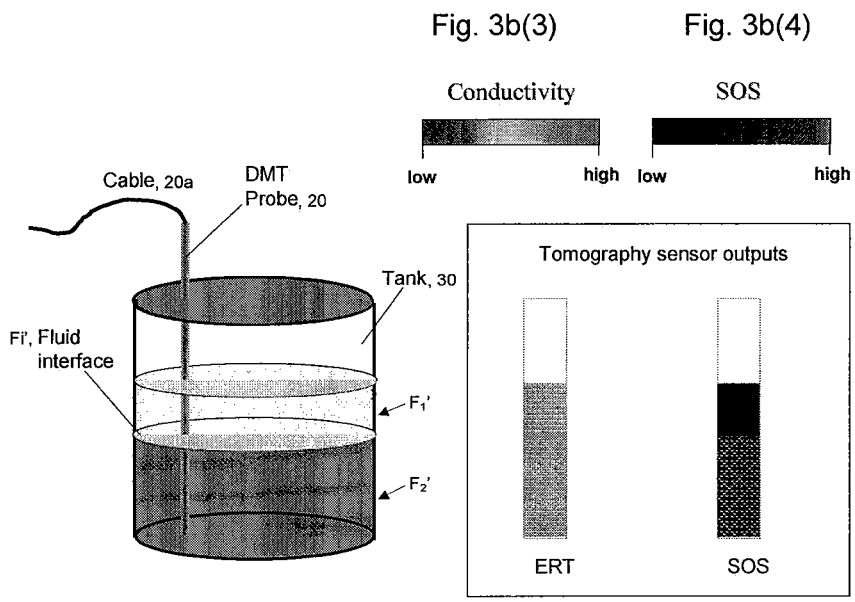
Fig. 3b(1)  Fig. 3b(2)

DUAL ACOUSTIC AND ELECTRICAL ANALYSIS TECHNIQUE FOR THE TOMOGRAPHIC DETERMINATION OF MULTIPHASE FLOWS IN PIPES AND/OR LIQUID/FROTH INTERFACES IN PROCESS TANKS

CROSS-REFERENCE TO RELATED APPLICATIONS

This application corresponds to international patent application serial no. PCT/US2013/028285, filed 28 Feb. 2013, which claims benefit to provisional patent application Ser. No. 61/604,080, filed 28 Feb. 2012, which is incorporated by reference in their entirety.

BACKGROUND OF THE INVENTION

Field of Invention

The present invention relates to techniques for analysis of mixing in multiphase flows in pipes and/or liquid/froth interfaces in process tanks or vessels; and more particular to techniques for determination of information about multiphase flows in pipes and/or liquid/froth interfaces in process tanks using tomographic techniques.

Description of Related Art

Tomographic approaches based on the use of Electrical Resistance Tomography (ERT), Electrical Capacitance Tomography (ECT) and Electrical Impedance Tomography (EIT) are becoming widely exploited in industrial processes for the analysis of mixing in multi-phase flows, liquid interfaces and liquid-froth layers for example.

These approaches are based on the difference in conductivity or electrical (complex) permeability of materials or mediums under investigation. Often the use of electrical analysis does not provide sufficient resolution of different materials to "see" the contrast between layers.

There is a need in the industry for a better way to "see" the contrast between layers of different materials, e.g., in multi-phase flows or process volumes.

SUMMARY OF THE INVENTION

According to some embodiments, the present invention may include, or take the form of, apparatus featuring a signal processor or processing module configured at least to:
  receive signaling containing information about at least two sensing modalities sensed by a single probe arranged in relation to a multiphase flow or process volume; and
  determine using a multiple modality tomographic analysis technique information about different fluid layers in the multiphase flow or process volume, based at least partly on the signaling received.

According to some embodiment of the present invention, the signal processor or processing module may be configured to provide corresponding signaling containing corresponding information about the different fluid layers in the multiphase flow or process volume.

The present invention may also include one or more of the following features:

The at least two sensing modalities may take the form of dual sensing modalities that include electrical and acoustic sensing modalities. The electrical sensing modality may be based at least partly on a difference in conductivity or electrical (complex) permeability of the multiphase flow or process volume under investigation. The acoustic sensing modality may be based at least partly on an acoustic speed of sound (SOS) analysis.

The signal processor or processing module may be configured to provide a differentiation between the "phases" of the multiphase flow or process volume, including that contained in a batch storage vessel, based at least partly on the signaling received.

The signal processor or processing module may be configured to determine a measurement of the different fluid layers in a tank, including a separator, e.g., of oil and water, or a flotation tank used in a mining separation and other multi-phase processes, based at least partly on the signaling received.

The apparatus may comprise the single probe, which may be configured as either a linear probe arranged in a separator, e.g., of oil and water, or a flotation tank, or a circumferential probe arranged around a pipe to analyze fluids flowing in the pipe, or around a storage tank or vessel.

The signal processor or processing module may be also configured to receive the signaling from a linear probe, e.g., having one side with a series of electrodes along the length thereof that may be used to conduct electrical resistance tomography (ERT), electrical capacitance tomography (ECT), or electrical impedance tomography (EIT) analysis of a fluidic medium surrounding the linear probe, and having another side with an array of acoustic transponders that may be configured to transmit and receive acoustic energy.

The array of acoustic transponders may be configured to operate as follows:
  each transponder may be configured an emitting transponder to provide sound waves, including acoustic or ultrasonic, and remaining transponders may be configured as responding transponders to detect signals and make respective measurements of associate acoustic transit times between respective emitting and responding transponders, so as to allow tomographic mapping of the fluidic medium based at least partly on a relative speed of sound (SOST) in different components, including different fluid layers, in a surrounding medium.

The signal processor or processing module may also be configured to base ERT and SOST tomographic images at least partly on a) ranges of electrical conductivity of the fluidic medium or materials, and b) densities of the fluidic medium or materials, respectively.

The signal processor or processing module may be configured to provide two independent views of the fluidic medium or materials system under analysis, based at least partly on the fact that electrical conductivity and density of a given fluidic medium, material or range of materials may have little or no direct correlation (in general), based at least partly on the signaling received.

The signal processor or processing module may be configured to provide enhanced resolution/differentiation in cases where the multiphase flow or process volume has two fluids of either different acoustic and electrical sensing modalities, or different acoustic sensing modalities and similar electrical sensing modalities, or similar acoustic sensing modalities and different electrical sensing modalities, based at least partly on the signaling received.

The signal processor or processing module may be configured to provide enhanced resolution/differentiation in cases where the multiphase flow or process volume has two fluids of either different densities and different electrical resistivities, or different densities and similar electrical resistivities, or similar densities and different electrical resistivities, based at least partly on the signaling received.

The signal processor or processing module may be configured to provide tomographic information that determines and resolves interface boundaries of multiphase flow or process volume, based at least partly on the signaling received.

The signal processor or processing module may be configured to provide corresponding signaling containing corresponding information about the different fluid layers in the multiphase flow or process volume, based at least partly on the signaling received.

The signal processor or processing module may be configured with at least one processor and at least one memory including computer program code, the at least one memory and computer program code configured, with the at least one processor, to cause the apparatus at least to receive the signaling and determine the different fluid layers in the multiphase flow or process volume, based at least partly on the signaling received.

The Method

According to some embodiments, the present invention may include, or take the form of, a method or process that includes steps for receiving with a signal processor or processing module signaling containing information about at least two sensing modalities sensed by a single probe arranged in relation to a multiphase flow or process volume; and determining with the signal processor or processing module using a multiple modality tomographic analysis technique information about different fluid layers in the multiphase flow or process volume, based at least partly on the signaling received.

The method may also include one or more of the features set forth herein, according to some embodiments of the present invention.

BRIEF DESCRIPTION OF THE DRAWING

The drawing includes FIGS. 1-3, which are not necessarily drawn to scale, as follows:

FIG. 1 is a block diagram of apparatus having a signal processor or processing module configured to implement some embodiments of the present invention.

FIG. 2 includes FIGS. 2a, 2b and 2c.

FIG. 2a is a diagram of side A of a dual modality tomographic (DMT) probe showing electrodes that form part of an ERT plane, according to some embodiments of the present invention.

FIG. 2b is a diagram of side B of a dual modality tomographic (DMT) probe showing acoustic transponders that form part of an SOST plane, according to some embodiments of the present invention.

FIG. 3 includes FIGS. 3a(1), 3a(2), 3a(3), 3a(4), 3b(1), 3b(2), 3b(3) and 3b(4).

FIG. 3a(1) is a diagram of a tank or vessel filled with two different fluids having different densities and electrical resistivities and a DMT probe arranged therein consistent with that shown in FIGS. 2a and 2b, according to some embodiments of the present invention.

FIG. 3a(2) is a diagram of tomography sensor outputs of the DMT probe shown in FIG. 3a(1), according to some embodiments of the present invention.

FIG. 3a(3) is a diagram in gray scale of conductivity from low to high of the DMT probe shown in FIG. 3a(1), according to some embodiments of the present invention.

FIG. 3a(4) is a diagram in gray scale of speed of sound (SOS) from low to high of the DMT probe shown in FIG. 3a(1), according to some embodiments of the present invention.

FIG. 3b(1) is a diagram of a tank or vessel filled with two different fluids having different densities and comparable electrical resistivities and a DMT probe arranged therein consistent with that shown in FIGS. 2a and 2b, according to some embodiments of the present invention.

FIG. 3b(2) is a diagram of tomography sensor outputs of the DMT probe shown in FIG. 3b(1), according to some embodiments of the present invention.

FIG. 3b(3) is a diagram in gray scale of conductivity from low to high of the DMT probe shown in FIG. 3b(1), according to some embodiments of the present invention.

FIG. 3b(4) is a diagram in gray scale of speed of sound (SOS) from low to high of the DMT probe shown in FIG. 3b(1), according to some embodiments of the present invention.

DETAILED DESCRIPTION OF BEST MODE OF THE INVENTION

FIG. 1: The Basic Apparatus 10

Figure 2C:
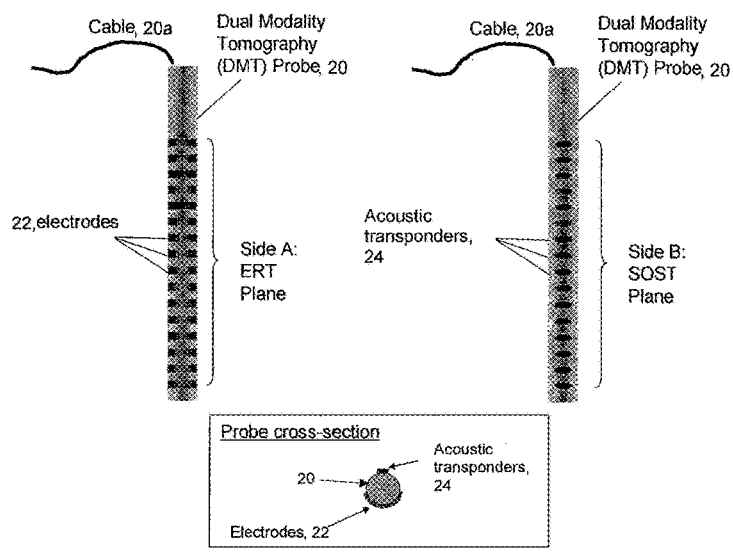
FIG. 2c is a diagram of a probe cross-section of the dual modality tomographic (DMT) probe in FIGS. 2a and 2b, according to some embodiments of the present invention.

FIG. 1 shows apparatus 10 having a signal processor or processing module 10a configured at least to
- receive signaling containing information about at least two sensing modalities sensed by a single probe, e.g., as shown in FIGS. 2-3, arranged in relation to a multiphase flow or process volume, e.g., as also shown in FIGS. 2-3; and
- determine using a multiple modality tomographic analysis technique information about different fluid layers in the multiphase flow or process volume, based at least partly on the signaling received.

The signal processor or processing module 10a may also be configured to provide corresponding signaling containing corresponding information about the different fluid layers in the multiphase flow or process volume. The scope of the invention is not intended to be limited to the type or kind of use of the corresponding signaling containing information about the different fluid layers in the multiphase flow or process volume, including for further processing, printing or displaying, as well as for other types or kinds of uses either now known or later developed in the future. Embodiments are also envisioned in which the corresponding signaling contains information that may be used for controlling the processing of the multiphase flow or process volume.

Further, the scope of the invention is not intended to be limited to the type or kind of multiphase flow or process volume being sensed by the single probe. For example, the scope of the invention is intended to include sensing multiphase flows or process volumes in tanks, vessels, pipes, etc., that are either now known or later developed in the future. Moreover, the scope of the invention is not intended to be limited to the type or kind of process of which the multiphase flow or process volume being sensed by the single probe forms part, including a process or processes that is or are either now known or later developed in the future.

The apparatus 10 may also include other circuits, components or modules 10b to implement the functionality of the signal processor or processing module 10a either now known or later developed in the future, e.g., including memory modules, input/output modules, data and busing architecture and other signal processing circuits, wiring or components, consistent with that known by a person skilled in the art, and/or consistent with that set forth herein.

FIG. 2

FIG. 2 shown a concept of using two sensing modalities on a single probe to provide enhanced tomographic imaging, according to some embodiments of the present invention.

In particular, and by way of example, a dual modality tomographic technique is disclosed herein which can be used to provide enhanced differentiation between "phases" of a multiphase flow or process volume (e.g., a batch storage vessel). The dual mode operation relies on the use of electrical probing (either conductivity or permeability) combined with acoustic speed of sound (SOS) analysis. This tomographic technique lends itself particularly well to the measurement of the different fluid layers, e.g., in a tank or vessel. Applications may include separators, e.g., of oil and water, flotation tanks used in mining separation, and/or other multi-phase processes either now know or later developed in the future.

The concept illustrated and disclosed herein for Dual Modality Tomographic (DMT) analysis is based on a single probe, e.g., that may take the form of a linear probe: Alternatively, and by way of example, it should be understood that this approach could equally well be implemented using the single probe in a circumferential mode around a pipe to analyze fluids flowing in a pipe, or around a storage vessel.

FIGS. 2a and 2b illustrate two sides A and B of a DMT linear probe 20, that is shown in FIG. 2c as circular in cross section, though other geometrical formats or shapes are possible and envisioned within the spirit of the present invention. In FIG. 2a, one side (A) is shown having a series of electrodes 22 along the length of the probe 20. These electrodes 22 are configured and used to conduct ERT, ECT, or EIT analysis of a medium (generally fluidic) surrounding the probe 20. (For example, the medium may take the form of the fluid in the tank 30 in FIGS. 3a(1) and 3b(1), consistent with that set forth below.) In FIG. 2b, the other side (B) is shown having an array of acoustic transponders 24 (e.g., which may take the form of devices that can transmit and receive acoustic energy). In operation, one of these transponders may be configured to emit sound waves (e.g., either acoustic or ultrasonic), and the signals may be detected by the remaining transponders to make a measurement of the acoustic transit time between the transponders. This may then be repeated for each transponder as an emitter. This allows tomographic mapping of the medium based on the relative speed of sound (SOST) in the different components (e.g. fluid layers) in the surrounding medium. The ERT and SOST tomographic images may be based or depend, e.g., on the following: a) the ranges of electrical conductivity of the materials, and b) the densities of the materials, respectively. As the electrical conductivity and density of a given material or range of materials may have little or no direct correlation (in a general sense), this approach can provide two independent views of the material system under analysis.

The DMT linear probe 20 may be configured with a cable 20a, e.g., for providing to the signal processor or processing module 10a (FIG. 1) the signaling containing information about the at least two sensing modalities sensed in order to determine using a multiple modality tomographic analysis technique information about different fluid layers in the multiphase flow or process volume, based at least partly on the signaling received.

FIG. 3

FIG. 3 shows the principles of operation according to some embodiments of the present invention. In particular, and by way of example, FIG. 3 further illustrates the principle of enhanced resolution/differentiation that is possible with a dual modality tomographic approach or technique, according to some embodiment of the present invention:

In FIG. 3a(1), a vessel or tank 30 is filled with two fluids $f_1$, $f_2$ of different densities, and different electrical resistivities, and a linear probe, e.g., like the DMT linear probe 20 shown in FIG. 2, is arranged therein. FIG. 3a(2) shows a conductivity mapping of the vessel or tank 30 that gives a view of the tank's contents, as the electrical conductivity changes at the boundary or fluid interface $f_i$ between the two fluids $f_1$, $f_2$. Likewise, FIG. 3a(2) also shows the speed of sound (SOS) tomography which yields a similar 'picture' of the tank's contents due to the change in sound speed at the liquid boundary or interface $f_i$.

In FIG. 3b(1), the vessel or vessel 30 is filled with two fluids $f_{1'}$, $f_{2'}$ of different densities, but comparable electrical resistivity, and a linear probe, e.g., like the DMT linear probe 20 shown in FIG. 2, is arranged therein. In this case, FIG. 3b(2) shows a conductivity mapping of the tank or vessel 30 that gives a uniform 'picture' of the tank's content, as the ERT technique shown on the left is unable to differentiate electrically the boundary between the fluids. However, the speed of sound (SOS) tomography shown on the right in FIG. 3b(2) results in a distinct visualization of the fluid boundary $f_{i'}$ as the sound proportional to density.

The approach according to the present invention can be used to provide better differentiation between materials or fluids that have similar properties in one of the sensing modalities but not in another sensing modality (which may generally be the case). It should be understood and appreciated by anyone skilled in the art that this concept may be further expanded to more than two sensing modalities.

Furthermore, the technique according to the present invention may provide additional tomographic information which may also improve the ability of such a system to resolve interface boundaries for example.

Signal Processor or Signal Processing Module 10a

By way of example, and consistent with that described herein, the functionality of the signal processor or processing module 10a may be implemented to receive the signaling, process the signaling, and/or provide the corresponding signaling, using hardware, software, firmware, or a combination thereof, although the scope of the invention is not intended to be limited to any particular embodiment thereof. In a typical software implementation, the signal processor or processing module 10a may include, or take the form of, one or more microprocessor-based architectures having a microprocessor, a random access memory (RAM), a read only memory (ROM), input/output devices and control, data and address busing architecture connecting the same. A person skilled in the art would be able to program such a microprocessor-based implementation to perform the functionality set forth herein, as well as other functionality described herein without undue experimentation. The scope of the invention is not intended to be limited to any particular implementation using technology either now known or later developed in the future. Moreover, the scope of the invention is intended to include a signal processor, device or module 10a as either part of the aforementioned apparatus, as a stand alone module, or in the combination with other circuitry for implementing another module.

Techniques for receiving signaling in such a signal processor or processing module 10a are known in the art, and the scope of the invention is not intended to be limited to any particular type or kind thereof either now known or later developed in the future. Based on this understanding, a person skilled in the art would appreciate, understand and be able to implement and/or adapt the signal processor or processing module 10a without undue experimentation so as to receive signaling containing information about at least two sensing modalities sensed by a single probe arranged in relation to a multiphase flow or process volume, consistent with that set forth herein.

Techniques, including techniques based on tomography or tomographic processing techniques, for determining information based on analyzing or processing signaling received in such a signal processor or processing module 10a are also known in the art, and the scope of the invention is not intended to be limited to any particular type or kind thereof either now known or later developed in the future. Based on this understanding, a person skilled in the art would appreciate, understand and be able to implement and/or adapt the signal processor or processing module 10a without undue experimentation so as to determine using a multiple modality tomographic analysis technique information about the about different fluid layers in the multiphase flow or process volume, based at least partly on the signaling received, consistent with that set forth herein.

It is also understood that the apparatus 10 may include one or more other modules, components, processing circuits, or circuitry 10b for implementing other functionality associated with the underlying apparatus that does not form part of the underlying invention, and thus is not described in detail herein. By way of example, the one or more other modules, components, processing circuits, or circuitry may include random access memory, read only memory, input/output circuitry and data and address buses for use in relation to implementing the signal processing functionality of the signal processor, or devices or components, etc.

Tomography or Tomographic Processing Techniques

Tomography or tomographic processing techniques are known in the art, and generally understood to refer to imaging by sections or sectioning, through the use of any kind of penetrating wave. A device used in tomography is called a tomograph, while the image produced is a tomogram. The method or technique is used, e.g., in radiology, archaeology, biology, geophysics, oceanography, materials science, astrophysics, quantum information and other sciences. In most cases, it is based on the mathematical procedure called tomographic reconstruction. Tomographic reconstruction algorithms are known in the art for determining the imaging by sections or sectioning, through the use of any kind of penetrating wave. By way of example, the reader is referred to U.S. Pat. Nos. 6,078,397; 5,181,778; 4,386,854; and 4,328,707, which all relate to tomographic techniques and are all incorporated by reference in their entirety. The scope of the invention is not intended to be limited to the type or kind of tomographic reconstruction algorithms, including those based at least partly on using ultrasonic waves, either now known or later developed in the future.

See also PCT application no. PCT/US12/52074, filed 23 Aug. 2012, which discloses an application based at least partly on using a tomography or tomographic processing technique, which was developed and is owned by the assignee of the instant patent application, and which is hereby incorporated by reference in its entirety.

See also PCT application no. PCT/US12/60811, filed 18 Oct. 2012, which discloses an application based at least partly on using a tomography or tomographic processing technique, which was developed and is owned by the assignee of the instant patent application, and which is hereby incorporated by reference in its entirety.

Moreover, the scope of the invention is intended to include using other types or kinds of tomography or tomographic processing technique either now known or later developed in the future. Finally, the scope of the invention is not intended to be limited to any particular type or kind of tomography or tomographic processing technique either now known or later developed in the future.

A person skilled in the art without undue experimentation would be able to adapt one or more of the aforementioned tomography or tomographic processing technique in order to implement the present invention, including to configure a signal processing module at least to receive signaling containing information about at least two sensing modalities sensed by a single probe arranged in relation to a multiphase flow or process volume; and determine using a multiple modality tomographic analysis technique information about different fluid layers in the multiphase flow or process volume, based at least partly on the signaling received, based at least partly on the signaling received.

Applications

The present invention may also be used in, or form part of, or used in conjunction with, industrial processes like a mineral extraction processing system for extracting or separating minerals in a fluidic medium that are either now known or later developed in the future, including any mineral process, such as those related to processing substances or compounds that result from inorganic processes of nature and/or that are mined from the ground, as well as including either other extraction processing systems or other industrial processes, where the extraction, or separating, or sorting, or classification, of product by size, or density, or some electrical characteristic, is critical to overall industrial process performance.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. Apparatus for determining information about "phases" in a multiphase flow or process volume, comprising:

a Dual Modality Tomographic (DMT) single probe configured to arrange in either a pipe having a multiphase flow or a process tank or vessel having a process volume, and also configured to sense at least two tomographic modalities that include electrical probing and speed of sound characteristics of the multiphase flow or the process volume, and provide signaling containing information about the at least two tomographic modalities sensed; and a signal processor or processing module configured at least to:

receive the signaling, and provide corresponding signaling containing information about different fluid layers in the multiphase flow or process volume using a DMT technique that combines an electrical probing and speed of sound analysis, based at least partly on the signaling received.

2. Apparatus according to claim 1, wherein the at least two tomographic modalities include electrical and acoustic tomographic modalities.

3. Apparatus according to claim 2, wherein an electrical tomographic modality is based at least partly on a difference in conductivity or electrical (complex) permeability of the multiphase flow or process volume under investigation.

4. Apparatus according to claim 2, wherein an acoustic tomographic sensing modality is based at least partly on an acoustic speed of sound analysis.

5. Apparatus according to claim 1, wherein the signal processing module is configured to determine a differentiation between the "phases" of the multiphase flow or process volume, including a batch storage vessel, based at least partly on the signaling received, and provide in the corresponding signaling information about the differentiation determined.

6. Apparatus according to claim 1, wherein the signal processor or processing module is configured to determine a measurement of different fluid layers in the process tank or vessel, including a separator of oil and water, or a flotation tank used in a mining separation, or other multi-phase processes, based at least partly on the signaling received, and provide in the corresponding signaling information about the measurement determined.

7. Apparatus according to claim 1, wherein the DMT single probe is configured as either a linear probe arranged in a separator of oil and water, or a flotation tank, or a circumferential probe arranged around a pipe to analyze fluids flowing in the pipe, or around a storage tank or vessel.

8. Apparatus according to claim 1, wherein the DMT single probe is a linear probe having one side with a series of electrodes along the length thereof that is used to conduct electrical resistance tomography (ERT), electrical capacitance tomography (ECT), or electrical impedance tomography (EIT) analysis of a fluidic medium surrounding the linear probe, and having another side with an array of acoustic transponders that are configured to transmit and receive acoustic energy.

9. Apparatus according to claim 8, wherein the array of acoustic transponders are configured to operate as follows:

each transponder is configured as an emitting transponder to provide sound waves, including acoustic or ultrasonic, and remaining transponders are configured as responding transponders to detect signals and make respective measurements of associate acoustic transit times between respective emitting and responding transponders, so as to allow tomographic mapping of the fluidic medium based at least partly on a relative speed of sound (SOST) in different components, including different fluid layers, in a surrounding medium.

10. Apparatus according to claim 9, wherein the signal processor or processing module is configured to base ERT and SOST tomographic images at least partly on a) ranges of electrical conductivity of the fluidic medium or materials, and b) densities of the fluidic medium or materials, respectively.

11. Apparatus according to claim 8, wherein the signal processor or processing module is configured to determine two independent views of the fluidic medium or materials system under analysis, based at least partly on the fact that electrical conductivity and density of a given fluidic medium, material or range of materials may have little or no direct correlation, based at least partly on the signaling received, and provide in the corresponding signaling information about the two independent views determined.

12. Apparatus according to claim 8, wherein the signal processor or processing module is configured to determine enhanced resolution/differentiation in cases where the multiphase flow or process volume has two fluids of either different acoustic and electrical tomographic modalities, or different acoustic tomographic modalities and similar electrical tomographic modalities, or similar acoustic tomographic modalities and different electrical tomographic modalities, based at least partly on the signaling received, and provide in the corresponding signaling information about the enhanced resolution/differentiation determined.

13. Apparatus according to claim 8, wherein the signal processor or processing module is configured to determine enhanced resolution/differentiation in cases where the multiphase flow or process volume has two fluids of either different densities and different electrical resistivities, or different densities and similar electrical resistivities, or similar densities and different electrical resistivities, based at least partly on the signaling received, and provide in the corresponding signaling information about the enhanced resolution/differentiation determined.

14. Apparatus according to claim 1, wherein the signal processor or processing module is configured to determine tomographic information that determines and resolves interface boundaries of multiphase flow or process volume, based at least partly on the signaling received, and provide in the corresponding signaling information about the tomographic information determined.

15. Apparatus according to claim 1, wherein the signal processor or processing module is configured with at least one processor and at least one memory including computer program code, the at least one memory and computer program code configured, with the at least one processor, to cause the signal processor or processing module at least to receive the signaling and determine the corresponding signaling containing information about the different fluid layers in the multiphase flow or process volume.

16. A method for determining information about "phases" in a multiphase flow or process volume, comprising:

arranging a Dual Modality Tomographic (DMT) single probe in either a pipe having a multiphase flow or a process tank or vessel having a process volume;

sensing with the DMT single probe at least two tomographic modalities that include electrical probing and speed of sound characteristics of the multiphase flow or the process volume, and providing signaling containing information about at least two tomographic modalities sensed; and receiving with a signal processor or processing module the signaling, and providing corresponding signaling containing information about different fluid layers in the multiphase flow or process volume using a DMT technique that combines an electrical probing and speed of sound analysis, based at least partly on the signaling received.

17. A method according to claim 16, wherein the at least two tomographic modalities include electrical and acoustic tomographic modalities.

18. A method according to claim 17, wherein an electrical tomographic modality is based at least partly on a difference in conductivity or electrical (complex) permeability of the multiphase flow or process volume under investigation.

19. A method according to claim 17, wherein an acoustic tomographic modality is based at least partly on an acoustic speed of sound analysis.

20. A method according to claim 16, wherein the method further comprises determining with the signal processor or processing module a differentiation between the "phases" of the multiphase flow or process volume, including a batch storage vessel, based at least partly on the signaling received, and providing in the corresponding signaling information about the differentiation determined.

21. A method according to claim 16, wherein the method further comprises determining with the signal processor or processing module a measurement of different fluid layers in the process tank or vessel, including a separator of oil and water, or a flotation tank used in a mining separation and other multi-phase processes, based at least partly on the signaling received, and providing in the corresponding signaling information about the measurement determined.

22. A method according to claim 16, wherein the method further comprises configuring or using the single probe as either a linear probe arranged in a separator of oil and water, or a flotation tank, or a circumferential probe arranged around a pipe to analyze fluids flowing in the pipe, or around a storage tank or vessel.

23. A method according to claim 16, wherein the method further comprises configuring the single probe as a linear probe having one side with a series of electrodes along the length thereof that is used to conduct electrical resistance tomography (ERT), electrical capacitance tomography (ECT), or electrical impedance tomography (EIT) analysis of a fluidic medium surrounding the linear probe, and having another side with an array of acoustic transponders that are configured to transmit and receive acoustic energy.

24. A method according to claim 23, wherein the method further comprises operating the array of acoustic transponders as follows:
each transponder is configured as an emitting transponder to provide sound waves, including acoustic or ultrasonic, and remaining transponders are configured as responding transponders to detect signals and make respective measurements of associate acoustic transit times between respective emitting and responding transponders, so as to allow tomographic mapping of the fluidic medium based at least partly on a relative speed of sound (SOST) in different components, including different fluid layers, in a surrounding medium.

25. A method according to claim 24, wherein the method further comprises configuring the signal processor or processing module to base ERT and SOST tomographic images at least partly on a) ranges of electrical conductivity of the fluidic medium or materials, and b) densities of the fluidic medium or materials, respectively.

26. A method according to claim 23, wherein the method further comprises determining with the signal processor or processing module two independent views of the fluidic medium or materials system under analysis, based at least partly on the electrical conductivity and density of a given fluidic medium, material or range of materials having little or no direct correlation, based at least partly on the signaling received, and providing in the corresponding signaling information about the two independent views determined.

27. Apparatus according to claim 23, wherein the method further comprises providing with the signal processor or processing module enhanced resolution/differentiation in cases where the multiphase flow or process volume has two fluids of either different acoustic and electrical tomographic modalities, or different acoustic tomographic modalities and similar electrical tomographic modalities, or similar acoustic tomographic modalities and different electrical tomographic modalities, based at least partly on the signaling received, and providing in the corresponding signaling information about the enhanced resolution/differentiation determined.

28. A method according to claim 23, wherein the method further comprises determining with the signal processor or processing module enhanced resolution/differentiation in cases where the multiphase flow or process volume has two fluids of either different densities and different electrical resistivities, or different densities and similar electrical resistivities, or similar densities and different electrical resistivities, based at least partly on the signaling received, and providing in the corresponding signaling information about the enhanced resolution/differentiation determined.

29. A method according to claim 16, wherein the method further comprises determining with the signal processor or processing module tomographic information that determines and resolves interface boundaries of multiphase flow or process volume, based at least partly on the signaling received, and providing in the corresponding signaling information about the tomographic information determined.

30. A method according to claim 16, wherein the method further comprises configuring the signal processor or processing module with at least one processor and at least one memory including computer program code, the at least one memory and computer program code configured, with the at least one processor, to cause the signal processor or processing module at least to receive the signaling and determine the corresponding signaling containing information about the different fluid layers in the multiphase flow or process volume.

* * * * *